United States Patent [19]

Koninckx

[11] Patent Number: 5,827,843

[45] Date of Patent: Oct. 27, 1998

[54] PREPARATION FOR SUBSTITUTION THERAPY, CONTAINING AT LEAST ONE PROGESTOGEN AND AT LEAST ONE ESTROGEN

[75] Inventor: Philippe Robert Marie Wilhelmus Ghislain Koninckx, Bierbeek, Belgium

[73] Assignee: Saturnus A.G., Luxembourg, Germany

[21] Appl. No.: 605,118

[22] PCT Filed: Sep. 8, 1994

[86] PCT No.: PCT/EP94/02997

§ 371 Date: Jun. 4, 1996

§ 102(e) Date: Jun. 4, 1996

[87] PCT Pub. No.: WO95/07081

PCT Pub. Date: Mar. 16, 1995

[30] Foreign Application Priority Data

Sep. 9, 1993 [NL] Netherlands ............................ 9301562

[51] Int. Cl.$^6$ .................................................. A61K 31/56
[52] U.S. Cl. ............................................................ 514/170
[58] Field of Search ................................................ 514/170

[56] References Cited

FOREIGN PATENT DOCUMENTS

| A275716 | 7/1988 | European Pat. Off. . |
| A279977 | 8/1988 | European Pat. Off. . |
| A346014 | 12/1989 | European Pat. Off. . |
| A559240 | 9/1993 | European Pat. Off. . |

*Primary Examiner*—Zohreh Fay
*Attorney, Agent, or Firm*—Webb Ziesenheim Bruening Logsdon Orkin & Hanson, P.C.

[57] ABSTRACT

The invention relates to a preparation for substitution therapy and oral contraception comprising at least one progestogen and at least one estrogen in which the estrogen dose varies with a periodicity such that blood loss is substantially avoided, wherein the periodicity is preferably less than 10 days, more preferably less than 7 days, such as preparations containing the progestogen and/or estrogen in an oral, transdermal, parenteral and/or implantable application form.

9 Claims, No Drawings

PREPARATION FOR SUBSTITUTION THERAPY, CONTAINING AT LEAST ONE PROGESTOGEN AND AT LEAST ONE ESTROGEN

This application is a 371 of PCT/EP94/62997 filed Sep. 8, 1994.

The present invention relates to a preparation for substitution therapy and for oral contraception. More particularly the present invention on the one hand relates to relieving the effects which occur because the ovaries decrease or stop production of female hormones, for instance during the menopause. The substitution therapy is mainly intended to induce amenorrhoea with negligible blood loss.

During and after the menopause these effects comprise hot flushes and nocturnal sweating, atrophy of the vagina which can result in sexual difficulties, bone decalcification, increase in heart and blood vessel disorders and psychic symptoms with a causal connection that is usually difficult to demonstrate.

Up to the present different types of substitution therapy have been applied comprising a hormone treatment with one or more estrogens and one or more progestogens.

According to a first therapy, low doses of estrogens and progestogens are administered, but such a treatment is ineffective in respect of the decalcification and heart and blood vessel disorders.

In another therapy the natural cycle of estrogens and progestogens is followed is closely as possible. This treatment inevitably results in menstruation and has the advantage of a reduced risk of cancer of the uterus.

According to yet another therapy only estrogens are administered in a dose which lies below the threshold for menstrual bleeding. This treatment has the drawback however of an increased risk of cancer of the uterus.

According to a most recently known therapy estrogens and progestogens are administered continuous] such that the endomotrium does not proliferate. This therapy has the drawback however of an unacceptably high incidence of slight, irregular blood loss.

The present invention has for its object to provide a substitution therapy wherein the above described drawbacks occur to a much lesser extent, with the objective of inducing amenorrhoea with negligible blood loss over a long period (many months to years).

On the other hand, the present invention relates to preparations designed for oral contraception with substantially continuous application.

In continuous application of oral contraceptive frequently intermediate bleedings occur. The preparations according to the present invention are designed to induce menstrual bleeding with a regular menstrual bleeding, with an extended cycle or eventually a constant amenorrhoea, but characterized by an optimal (cycle) control and/or by a substantially reduced ocurrence of intermediate bleeding.

EP-A-559 240 discloses preparations for substitution therapy and oral contraception in which the estrogen dose is constant and the progestagen dose is periodically alternated.

However, the improvement in inhibiting endometrium blooding is minor. Above that, since the use of higher progestogen doses provided better results than lower doses it appears illogical to use periodically varying estrogen doses.

The present invention is based on the finding that suprisingly when using periodically varying estrogen doses the occurence of blood loss and intermediate bleeding is substantially avoided. The estrogen dose is herein oscillated such that estrogen-dominant and progestogen-dominant periods occur alternatingly with a sufficiently short periodicity. This short periodicity in the estrogen dose is necessary to avoid blood loss.

Purely by administering a dose of progestogen or estrogen substantially constant in time and an estrogen or progestogen varying in time between at least two dose levels, it was possible to induce the desired amenorrhoea while no blood loss occurred over a longer period.

The invention therefore relates to a preparation for substitution therapy and for oral contraception comprising at least one progestogen and at least one estrogen in which the estrogen dose varies with a periodicity such that blood loss is substantially avoided.

It is noted that the preparation is formulated such that a substantially constant blood concentration is obtained for progestogen or estrogen, while the estrogen concentration in the blood varies between two blood concentrations. The periodicity must be sufficiently short and is generally less than 10 days. The periodicity is usually less than 7 days. The periodicity generally lies between 2–9 days, preferably between 2–6 days. It will however be apparent that the periodicity is dependent on the estrogens and progestogens used and the applied doses. Both the periodicity and concentrations of estrogen and progestogen are easy to determine by routine experimentation.

According to an embodiment of the invention the preparation contains a constant progestogen dose, while the estrogen dose oscillates between two levels. This preparation is recommended because there is a greater certainty of avoiding blood loss over a longer period.

According to another embodiment the preparation contains oscillating doses of progestogen and estrogen, in varying ratios however such that blood loss is avoided and amenorrhoea is induced.

Use can be made in general of all known progestogens, such as

| progesterone | 300–900 mg/day |
| norethisterone acetate | 2–5 mg/day |
| medroxyprogesterone acetate | 1–5 mg/day |
| d-norgestrel | 30–150 µgr/day |
| desogestrel | 30–150 µgr/day |
| norgestimate | 30–150 µgr/day |
| cyproterone acetate | 0.2–2 mg/day, |
| gestodene | 10–150 µg/day |
| 3-ketodesogestrel | 10–150 µg/day |
| drospirenon | 0.2–3.0 mg/day | or combinations thereof. It is noted that the preparation can contain one or more progestogens and estrogens.

It will be apparent that the quantity of progestogen and estrogen depends on the person (constitution and age), the progestogen(s) and estrogen(s), anti-progestogen and anti-estrogen for use and the form of administering same.

The progestogen and estrogen can each be present in an oral, transdermal, parenteral or implantable application form for substitution therapy. The preparation can for instance comprise an application form which contains the progestogen and estrogen, and a second like application form which contains the progestogen and an increased dose of estrogen. The progestogen and estrogen can of course be present in like but separate forms of application or in mutually differing forms of application. The progestogen can for instance be an implantable application form while the estrogens is administered orally, transdermally or parenterally in a dose which takes account of the required time period according to the invention.

The oral application form to be used comprises tablets, capsules, syrup, solutions. The transdermal forms of application comprise gels, plasters. Strips can for instance be used wherein tablets with progestogen and estrogens in the desired ratio and periodicity are arranged in time sequence. The parenteral application form comprises injection fluid and the like. The implantable application form comprises for example a known implantable sustained release preparation.

The preparations for oral contraceptive comprise estrogens and progestogens in common form.

Preparations according to the invention were administered over a period of 3–12 months to 40 women in the menopause. By making use of the combination preparations according to the invention a constant amenorrhoea could be obtained in the case of more than 90% of the women, wherein the clinical tolerance was perceived as optimal, wherein the woman did not discern any subjective difference between a fixed or changing estrogens dose with a periodicity of about one week.

Using the preparations according to the invention as oral contraceptive intermediate bleeding will be substantially reduced.

EXAMPLE 1

A preparation according to the invention comprised tablets of the type A which contained 10 gamma aethinyl-estradiol, 1 mg estradiol valerianate and 0.5 mg norethisterone, and tablets of the type B which contained 15 gamma instead of 10 gamma aethinyl-estradiol. By alternatingly administering the tablets A and B over a time period of 7 days an amenorrhoea could be induced without blood loss for a very long period of time.

EXAMPLE 2

A preparation according to the invention contained 1 mg norethisterone or 0.5 mg cyproterone acetate and 2 mg estradiol valerianate. The preparation moreover contained tablets of the type B having 3 mg instead of 2 mg estradiol valerianate. By using the preparation with alternate administering (4–5 days) of the tablets A and B or B and A an amenorrhoea could be induced without blood loss for a longer period of time.

EXAMPLE 3

A preparation according to the invention comprised tablets of the type A which contained 15 gamma aethinyl-estradiol and 1 mg estradiol valerianate and 1 mg norethisterone. The preparation moreover contained tablets of the type B having 1.5 mg instead of 1 mg norethisterone. By alternatingly administering the tablets A and B with a periodicity of 4–7 days an amenorrhoea could be induced without blood loss for a very long period of time.

EXAMPLE 4

A preparation according to the invention for oral contraceptive with optimal cycle control comprises tablets of type A comprising 20 μg aethinyl-estradiol and 75 μg gestoden. The preparation contained tablets of type B comprising 30 μg instead of 20 μg aethinyl-estradiol. Tablets A and B are used in four alternating periods of six days.

EXAMPLE 5

A preparation according to the invention for oral contraceptive with optimal cycle control comprises tablets of type A comprising 15 μg aethinyl-estradiol and 75 μg gestoden, and tablets of type B comprising 25 μg instead of 15 μg aethinyl-estradiol. Tablets A and B are used in six alternating periods of four days.

In example 4 and 5 only aethinyl-estradiol is used in order to use a estrogen dose which is as low as possible. However, higher estrogen doses may be used. Instead of using a constant progestogen dose fluctuating doses may be use fluctuating simultaneously and/or progressively in view of the varying estrogen dose.

EXAMPLE 6

A preparation for oral contraceptive according to the invention comprises tablets of type A comprising 20 μg aethinyl-estradiol and 75 μg gestoden, and tablets of type B comprising 30 μg aethinyl-estradiol and 75 μg gestoden and 50 μg onapristone. The tablets A and B are used in four alternating periods of each six days. After four periods the whole cycle is repeated without allowing a free period.

EXAMPLE 7

A preparation according to the invention for hormone substitution treatment comprises tablets of type A comprising 2 μg estradiol valerianate and 50 μg gestoden. The tablets of type B comprised 3 μg estradiol valerianate and 25–100 μg onapristone. By alternatingly administering the tablets A and B over a time period of seven days amennorrhoea could be induced without blood loss for a very long period of time.

It is obvious for a skilled person in the examples in association with intermittently given antiprogestogen or anti-estrogen can be alternated alone or simultaneously with estrogens and/or progestagens. For instance, the antiprogestagen is added in a constant dose to the actual and the above mentioned combinations of estrogens and progestagens in products for hormone replacement therapy and for contraception.

I claim:

1. Preparation for substitution therapy and for oral contraception comprising at least one progestogen and at least one estrogen having dosing means in association therewith wherein the progestogen dose is substantially constant and the estrogen dose varies to oscillate between an estrogen-dominant period and a progestogen-dominant period with a periodicity of less than 10 days such that blood loss is substantially avoided.

2. Preparation as claimed in claim 1, wherein said periodicity amounts to 2–9 days.

3. Preparation as claimed in claim 1, wherein the dose of progestogen is substantially constant and the dose of estrogen oscillates.

4. Preparation as claimed in claim 1, wherein the dose of progestogen and the dose of estrogen oscillate in such a dose ratio that blood loss is substantially avoided.

5. Preparation as claimed in claim 1, wherein the progestogen comprises

| | |
|---|---|
| progesterone | 300–900 mg/day |
| norethisterone acetate | 0.2–5 mg/day |
| medroxyprogesterone acetate | 1–5 mg/day |
| d-norgestrel | 30–150 μgr/day |
| desogestrel | 30–150 μgr/day |
| norgestimate | 30–150 μgr/day |
| cyproterone acetate | 0.2–2 mg/day, |

-continued

| | |
|---|---|
| gestodene | 10–150 µg/day |
| 3-ketodesogestrel | 10–150 µg/day |
| drospirenon | 0.2–3.0 mg/day | or combinations thereof.

6. Preparation as claim 1, wherein the estrogens comprises

| | |
|---|---|
| aethinylestradiol | 5–15 gamma/day |
| oestradiol valerianate | 1–4 mg/day |
| oestradiol | 1–2 mg/day |

-continued

| | |
|---|---|
| conjugated oestrogen | 0.3–1.25 mg/day |
| oestriol | 1–4 mg/day, | or combinations thereof.

7. Preparation as claimed in claim 1, further comprising anti-progestogen.

8. Preparation as claimed in claim 1, further comprising anti-estrogen.

9. Preparation as claimed in claim 1, further containing the progestogen and/or estrogen in an oral, transdermal, parenteral and/or implantable application form.

* * * * *

UNITED STATES PATENT AND TRADEMARK OFFICE
CERTIFICATE OF CORRECTION

PATENT NO.   : 5,827,843
DATED        : October 27, 1998
INVENTOR(S)  : Philippe R.M.W.G. Koninckx It is certified that error appears in the above-identified patent and that said Letters Patent is hereby corrected as shown below:

Column 1 Line 29 "is closely as possible" should read --as closely as possible--.

Column 1 Line 37 "continuous]" should read --continuously--.

Column 1 Line 38 "endomotrium" should read --endometrium--.

Column 1 Line 60 "blooding" should read --bleeding--.

Column 5 Line 9 Claim 6 "as claim 1" should read --as claimed in claim 1--.

Column 5 Line 9 Claim 6 "estrogens comprises" should read --estrogen comprises--.

Signed and Sealed this

Twenty-ninth Day of June, 1999

Attest:

Q. TODD DICKINSON

*Attesting Officer*            *Acting Commissioner of Patents and Trademarks*